United States Patent
Marullo et al.

(10) Patent No.: US 6,645,755 B1
(45) Date of Patent: Nov. 11, 2003

(54) VECTOR MODIFIED BY SEQUENCE CODING FOR A SEQUENCE OF AMINO ACIDS CONTAINED IN A MAMMALIAN PROTEIN HAVING THE BIOLOGICAL ACTIVITY OF A MEMBRANE RECEPTOR, EXPRESSION OF THIS SEQUENCE IN TRANSFORMED UNICELLULAR CULTURES BY MEANS OF THIS VECTOR, PROCEDURE FOR STUDYING LIGANDS RECOGNIZING THESE RECEPTORS

(75) Inventors: Stefano Marullo, Paris (FR); Colette Delavier, Paris (FR); Laurent Emorine, Paris (FR); Donny Strosberg, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 08/422,612

(22) Filed: Apr. 13, 1995

Related U.S. Application Data

(63) Continuation of application No. 08/015,923, filed on Feb. 10, 1993, now abandoned, which is a continuation of application No. 07/675,110, filed on Mar. 25, 1991, now Pat. No. 5,242,822, which is a continuation of application No. 07/324,890, filed on Mar. 17, 1989, now abandoned.

(30) Foreign Application Priority Data

Mar. 21, 1988 (FR) .............................. 88 03475

(51) Int. Cl.⁷ .............................. C12N 1/14; C12N 1/16; C12N 1/18
(52) U.S. Cl. .............................. 435/254.2; 435/254.21; 435/254.22; 435/254.3
(58) Field of Search .............................. 435/69.1, 252.3, 435/320.1, 254.2, 254.21, 254.22; 436/501

(56) References Cited

U.S. PATENT DOCUMENTS

| | | | |
|---|---|---|---|
| 4,615,974 A | 10/1986 | Kingsman et al. | .......... 435/69.1 |
| 4,859,609 A | * 8/1989 | Dull et al. | .................. 436/501 |
| 5,482,835 A | * 1/1996 | King et al. | ..................... 435/6 |

FOREIGN PATENT DOCUMENTS

EP 0244221 11/1987

OTHER PUBLICATIONS

PNAS 84:4332–4336, Jun. 1987, Lübbert et al CDNA cloning of a serotonin 5-HT1C receptor by electrophysician assays of MRNA-injected Xenopus oocytes.*
Burkholder et al. "The yeast alpha-factor receptor: structural properties deduced from the sequence of the STE2 gene." Nucleic Acids Research 13(23):8463–8475, 1985.*
Strosberg, "Biotechnology of β-Adrenergic Receptors", Molecular Neurobiology, 4:211–250 (1990).
Strosberg et al., "Functional Expression of Receptors in Microorganisms," Trends in Pharmacological Sciences, 13:95–98 (Mar. 1992).
Freissmuth et al., "Expression of Two Human β-Adrenergic Receptors in *Escherichia coli*: Functional Interaction With Two Forms of the Stimulatory G Protein," Proc. Natl. Acad. Sci. USA, 88:8548–8552 (1991).
Tate et al., "Expression of Three Human β-Adrenergic-Receptor: Subtypes in Transfected Chinese Hamster Ovary Cells," Eur. J. Biochem., 196:357–361 (1991).
Marullo et al., "Human β-2-Adrenergic Receptors Expressed in *Escherichia coli* Membranes Retain Their Pharmacological Properties," Proc. Natl. Acad. Sci. USA, 85:7551–7555 (1988).
Marullo et al., "Expression of Human β-1 and β-2 Adrenergic Receptors in *E. coli* as a New Tool for Ligand Screening," Bio/Technology, 7:923–926 (1989).
Breyer et al., "Mutational Analysis of Ligand Binding Activity of β-2 Adrenergic Receptor Expressed in *Esherichia coli*," EMBO J., 9:2679–2684 (1990).
Chapot et al., "Localization and Characterization of Three Different β-Adrenergic Receptors Expressed in *Escherichia coli*," Eur. J. Biochem., 187:137–144 (1990).
Marullo et al., "Selective Binding of Ligands to β-1 and β-2 or Chimeric β-1/β-2-Adrenergic Receptors Involves Multiple Subsites," EMBO J., 9:1471–1476 (1990).
Luyten et al., "Comparative Study of the Binding Properties of Cloned Human β-1 and β-2-Adrenergic Receptors Expressed in *Escherichia coli*," Drug Investigation 3 (Suppl. 1):3–12 (1991).
King et al., "Control of Yeast Mating Signal Transduction by a Mammalian β-2-Adrenergic Receptor and Gs α Subunit," Science, 250:121–123.
Galli et al., "Replica Filter Assay of Human β-Adrenergic Receptors Expressed in *E. coli*," Biochemical and Biophysical Research Communications, 173:680–688 (1990).
Freissmuth et al., "Expressions of Two Human β-Adrenergic Receptors in *E. coli*: Functional Interaction with Two Forms of Gs" (Abstract).

(List continued on next page.)

*Primary Examiner*—Yvonne Eyler
(74) *Attorney, Agent, or Firm*—Finnegan, Henderson, Farabow, Garrett & Dunner, L.L.P.

(57) ABSTRACT

The invention relates to a vector capable of being replicated in cultures of unicellular organisms, this vector containing a gene coding for a eukaryotic protein having the biological activity of a membrane receptor and interacting with a regulatory protein—called the G protein—able to bind molecules of guanosine triphosphate (GTP). The invention also relates to cell organisms transformed by the above vectors. It also relates to procedures for the detection of the capacity of a molecule to behave as a ligand for a receptor and a procedure for studying the affinity of a receptor for a ligand as well as a kit for detecting the possible affinity of a ligand for a receptor.

21 Claims, 8 Drawing Sheets

OTHER PUBLICATIONS

Bertin et al., "Expression and Characterization of a Functional Human Serotonin 5–HT1A Receptor in *Escherichia coli*" (Abstract).

Dohlman et al., "A Family of Receptors Coupled to Guanine Nucleotide Regulator Proteins," Biochem., 26:2657–2664 (1987).

Dietzel et al., "The Yeast SCG1 Gene: A Gα–like Protein Implicated in the a– and α–Factor Response Pathway," Cell, 50:1001–1010 (1987).

Peralta et al., "Primary Structure and Biochemical Properties of an M2 Muscarinic Receptor," Science, 236:600–605 (1987).

Maniatis et al., Molecular Cloning: A Laboratory Manual, Cold Spring Harbor (1982).

Kobilka et al., "Delineation of the Nature of the Genes for the Human and Hamster β2 Adrenergic Receptor," J. of Biol. Chem., 262(15):7321–7327 (1987).

Bonner et al., "Identification of a Family of Muscarinic Receptor Genes," Science, 237:527–532 (1987).

Yarden et al., "The Avian β–Adrenergic Receptor: Primary Structure and Membrane Topology," Proc. Natl. Acad. Sci. USA, 83:6795–6799 (1986).

Dixon et al., "Cloning of the Gene and cDNA for Mammalian β–Adrenergic Receptor and Homology with Rhodopsin," Nature, 321:71–79 (1986).

George et al., "Molecular Cloning of a Human cDNA Encoding a Polypeptide with Structural Homology to the Hamster Lung β–Adrenergic Receptor," Fed. Proc., 46:2193 (1987).

Frielle et al., "Cloning of the cDNA for the Human β–1–Adrenergic Receptor," Proc. Natl. Acad. Sci. (USA), 84:7920–7924 (1987).

Kobilka et al., "Cloning, Sequencing, and Expression of the Gene Coding for the Human Platlet α2–Adrenergic Receptor," Science, 238:650–656 (1987).

Kubo et al., "Cloning Sequence and Expression of Complementary DNA Encoding the Muscarinic Acetylocholine Receptor," Nature, 323:411–416 (1986).

Emorine et al., "Structure of the Gene for Human β2–Adrenergic Receptor: Expression and Promoter Characterization," Proc. Natl. Acad. Sci. (USA), 84:6995–6999 (1987).

Levitan, E., "Cloning of Serotonin and Substance K Receptors by Functional Expression in Frog Oocytes," Trends in Neurosciences, 11:41–43 (1988).

* cited by examiner

VECTOR MODIFIED BY SEQUENCE CODING FOR A SEQUENCE OF AMINO ACIDS CONTAINED IN A MAMMALIAN PROTEIN HAVING THE BIOLOGICAL ACTIVITY OF A MEMBRANE RECEPTOR, EXPRESSION OF THIS SEQUENCE IN TRANSFORMED UNICELLULAR CULTURES BY MEANS OF THIS VECTOR, PROCEDURE FOR STUDYING LIGANDS RECOGNIZING THESE RECEPTORS

This application is a continuation of application Ser. No. 08/015,923 filed Feb. 10, 1993, now abandoned, which is a continuation of application Ser. No. 07/675,110, filed Mar. 25, 1991 now U.S. Pat. No. 5,242,822, which is a continuation of application Ser. No. 07/324,890 filed Mar. 17, 1989 now abandoned.

The invention relates to a vector which can be replicated in cultures of unicellular organisms, this vector containing a gene coding for a eucaryotic protein having the biological activity of a membrane receptor and interacting with a regulatory protein—called G protein—capable of binding molecules of guanosine triphosphate (GTP).

The invention also relates to unicellular organisms transformed by genes coding for these membrane receptors and bearing at their surface peptide sequences recognized by specific ligands of the membrane receptors.

The invention also relates to kits for the identification of mammalian proteins which have properties making it possible to verify whether they belong to a family of mammalian membrane receptors or, conversely, to study the degree of affinity of certain substances for specific membrane receptors.

Generally speaking, the G proteins are proteins having the capacity to interpose themselves structurally and functionally between receptors and enzymes catalyzing the production of intracellular mediators (such as adenylate cyclase, guanylate cyclase, the phospholipases, the kinases) or between receptors and ionic channels, the controlled opening of which leads to a flux of ions (such as calcium, potassium, sodium and hydrogen ions) into the cell.

These proteins have transduction and coupling functions and are characterized by a monomeric structure composed of three protein subunits alpha, beta, gamma. Different G proteins can be distinguished on the basis of variations observed in their alpha subunit and sometimes in their beta subunit. These G proteins have been described in detail in the article by Allen M. Spiegel (21).

Membrane receptors of mammalian cells normally coupled to a G protein have been identified by cloning, supplemented by the analysis of their sequence in the case of some of them. These receptors include regions exposed at the surface of the host cells which have specific affinities for a large variety of ligands, hormones, neurotransmitters and other sensory stimulants capable of transmitting signals to the interior of these cells via the corresponding receptors and the G proteins.

Receptors of interest in the context of the invention are, in particular, the following receptors:

β-adrenergic receptors: (β1 avian receptor, β1 and β2 mammalian receptors), receptors for glucagon, the adrenocorticotropic hormone, the parathyroid hormone (PTH), the thyroid-stimulating hormone, the growth hormone releasing factor, prostaglandin E, D1 dopaminergic receptors, the intestinal vasoactive peptide receptor, the mucarinic receptors M1 to M6, the S1 and S2 serotonin receptors, the D2 dopaminergic receptor, the receptors for the neuropeptide substance K, vasopressin, somatostatin, bombesin, cholecystokinin (CCK), light receptors, the receptor for the chemotactic peptide Met-Leu-Phe, the α adrenergic receptors (α1, α2), the H1 histamine receptor, the opioid receptor (enkephalins, endorphins), the receptors for the neuropeptide substance P, angiotensin II, prostaglandin, the corticotropic hormone releasing factor, bradykinin, secretin and the olfactory receptors.

A preferred family of receptors according to the invention which possess genetic and molecular properties which are essentially common to all of them, comprises β1, β2, α1 and α2-adrenergic receptors (1) (2) (3) (4), muscarinic receptors belonging to the subtypes M1 to M4 (5) (6) and the receptor for the neuropeptide known as "substance K" (7). These receptors appear to possess a common structural organization within the plasma membrane, usually characterized by seven hydrophobic transmembrane segments between which are inserted extra- and intra-cellular loops, by an extracellular amino-terminal region and by a cytoplasmic carboxyl-terminal region.

Several genes coding respectively for some of these receptors have been made capable of expressing themselves after their introduction into cultures of mammalian cells belonging to foreign species. The operations of transformation necessary for the expression of these genes in mammalian cells belonging to foreign species are quite complex and cannot easily be discussed in terms of the expression of other receptors.

The aim of the invention is to furnish procedures and agents making it easy to identify and study new membrane receptors exhibiting structural characteristics in common with the membrane receptors of the type indicated above. Conversely, the aim of the invention is to facilitate the study of the possible degree of affinity of molecules capable of behaving as ligands with respect to these membrane receptors.

In particular, the invention relates to a vector, which can replicate in a culture of a host cell, containing a nucleotide insert coding for a sequence of amino acids contained in a mammalian protein and having the biological activity of a membrane receptor, this vector being characterized in that the insert is placed under the control of a sequence included in this vector allowing the expression of this insert in the host cell, and in particular including a promoter recognized by the polymerases of this unicellular host, and in that this insert codes for a sequence of amino acids contained in a protein possessing structural elements in common with the above-mentioned membrane receptors, in particular the α- or β-adrenergic receptors, the muscarinic receptors, the neuropeptide receptors, in particular for "substance K".

The invention is the result of the discovery that placing a sequence of nucleotides coding for a mammalian membrane receptor under the control of a promoter recognized by the polymerases of unicellular host under conditions which allow the expression of this sequence of nucleotides within the unicellular organism also makes possible, when this expression occurs, the transport of the expressed product into the membranes of the unicellular host, and that this expression is also accompanied by the exposure, also at the exterior of these unicellular hosts, of sites characteristic of the membrane receptors which appear at the surface of the cells of mammalian origin, and do so in a spatial configuration that is conserved at the molecular level such that these sites can be recognized by the same ligands.

By "unicellular host" is understood any organisms capable of being maintained in culture in the absence of cellular differentiation. The unicellular organism of choice is constituted by *Escherichia coli*. However, other microorganisms can be used with equal facility, provided of course that vectors are known for each of them, especially of the plasmid type, which are capable of self replication and nucleotide sequences which can be inserted into these vectors and which are capable, when they are followed in these vectors by an insert coding for a polypeptide having the properties of a membrane receptor under the conditions indicated above, of insuring the expression of this insert in the selected organisms and its transport into the membranes of these unicellular hosts.

In the case where the expression is to be carried out in *E. coli*, the sequence directing the expression of the insert may include, for example, the elements of regulation, in particular the promoter of the lactose operon or the tryptophan operon.

Other unicellular microorganisms capable of being used and, consequently, other vectors which can themselves be modified by a sequence capable of directing the expression of a membrane receptor or similar structure in these unicellular organisms are indicated in the table below:

| Unicellular Organism | Vector type | Promoter region |
|---|---|---|
| S. Cerevisiae | plasmid 2µ | alcohol dehydrogenase I (ADH. I) |
| S. Cerevisiae | plasmid PBM 258 | galactokinase promoter gene (GAL I) |

The above-mentioned organisms and the corresponding, modified vectors advantageously lend themselves to the expression of genetic sequences coding for molecules having structural properties in common with mammalian membrane receptors already known, and to their transport to the membrane of these unicellular hosts under the conditions indicated above.

As examples of receptors likely to be introduced and expressed into unicellular organisms, in particular *E. coli*. mention should be made of:
- the different β-adrenergic and muscarinic receptors described in the chapter entitled "the β-adrenergic receptors and G-proteins" by A. D. Strosberg in the monograph edited by the same author under the title "The Molecular Biology of Receptors—Techniques and Applications of Receptor Research" and published by Ellis Horvood Ltd. Chichester—Great Britain (VCH)
- or also the receptors described in the publications of Brian K. Kobilka et al., Nature, Vol. 329, 75–79 of Sep. 3, 1987 or of L. J. Emorine et al., Proc. Natl. Acad. Sci. USA, vol. 84, p. 6995–6999 of, October 1987.

The invention makes possible not only the study of the mammalian membrane receptors which have been specified but also those of the receptors or polypeptides having similar structural elements which can be prepared or purified starting from standard techniques, for example
- either by means of cDNAs obtained by reverse transcription of mRNA and sequenced for example according to the techniques described by Dixon, R. A. F. et al. (1986) Nature, 321, 75, Dixon, R. A. F. et al. (1987) Nature, 326, 73, Yarden, Y. et al. (1987) Proc. Natl. Acad. Sci. USA 83, 6795–6799,
- or by having recourse to oligonucleotides used as hybridization probes which make it possible to isolate polynucleotides coding for receptors of the gene in question according to known techniques, including selective hybridization reactions.

These probes consist, for example, of oligonucleotide probes derived from fragments of DNA from regions showing strong homologies between the different receptors.

Probes which can be used to isolate nucleotide sequences coding for membrane receptors can also, for example, consist of conserved fragments, obtained from nucleotide sequences coding for one of the seven hydrophobic transmembrane peptide sequences shown on pages 148–149 of the monograph edited by A. D. Strosberg already cited. These different peptide sequences indicated by the roman numerals I to VII and quite similar to each other are derived from hamster β2-adrenergic receptors, human β-adrenergic receptors, turkey β-adrenergic receptors, acetyl choline muscarinic receptors from pig brain and bovine opsin.

In the case of bovine opsin, recourse can be made to the cDNA corresponding to the genomic RNA of the receptor in order to prepare one of the probes previously mentioned.

As an illustration, the following probes can be used to isolate nucleotide sequences coding for membrane receptors.

CTTGGTCAGCTTGGCCTGTGCTGATCTGG-TCATG    (transmembrane segment II)

GCTTTCATGGTCAGCTGGCTGC-CCTAC    (transmembrane segment VI)

Sets of probes which can be represented by the following general formulae can also be used:

transmembrane II sets:

$$5'X_1X_2TX_3X_4TX_5X_6X_7CX_8TGGCX_9X_{10}X_{11}X_{12}GCTGAX_{13}\text{-}CTX_{14}X_{15}TX_{16}ATG3'$$

in which $X_1$ to $X_{16}$ have the following meanings, which can be varied independently in each case:
$X_1$ is C or T
$X_2$ is T or A
$X_3$ is G or C
$X_4$ is G or T
$X_5$ is C or G
$X_6$ is A or T
$X_7$ is G or C
$X_8$ is T or C
$X_9$ is C or G
$X_{10}$ is T or G
$X_{11}$ is G or T
$X_{12}$ is T or G
$X_{13}$ is T or C
$X_{14}$ is G or C
$X_{15}$ is G or T
$X_{16}$ is C or G and transmembrane VI sets;

$$5'GCY_1TTCATY_2Y_3TY_4Y_5Y_6CTGGY_7TY_8CCY_9TY_{10}C3'$$

in which $Y_1$ to $Y_{10}$ are independently assigned the following meanings:
$Y_1$ is T or G
$Y_2$ is G or C
$Y_3$ is G or C
$Y_4$ is C or G
$Y_5$ is A or T
$Y_6$ is G or C
$Y_7$ is C or G
$Y_8$ is G or C
$Y_9$ is C or G
$Y_{10}$ is A or T In order to isolate nucleotide sequences presumed to code for a membrane receptor, use will preferably be made of two or more probe sequences such as those defined above chosen for their relatedness to different regions of the nucleotide sequences presenting a set of sequences in part corresponding to the seven transmembrane segments described above. In particular, use will be made of probes of the types described above with their respective complementary sequences.

Recourse may also be made to sets of these probes.

It can be seen that the procedure according to the invention makes it possible to measure for each membrane receptor expressed at the surface of a unicellular organism, in particular bacteria, the degrees of affinity of different molecules presumed to behave as ligands for these receptors. Moreover, these ligands can also be used to locate within different transformed colonies a large number of fragments of nucleic acid of various origins (the so-called "shot gun" approach), including fragments coding for these mammalian polypeptides. This will lead to the detection of those colonies which, on account of the expression of a sequence coding for the mammalian membrane receptor, form a bond with the corresponding ligand.

Conversely, the invention also makes possible the study of the affinity of various types of molecules for a specific membrane receptor consisting of the expression of a corresponding insert in a vector modified under the conditions defined above and incorporated in a cell host in which this vector can be replicated.

Similarly, the invention makes it possible to compare the mutual affinities of a specific receptor and different molecules possessing elements of structure in common with different mammalian membrane receptors, hence the possibility of classifying the receptors in terms of order of affinity. Any suitable ligand may be used in these comparative assays. As examples of ligands mention should be made of pindolols, iodocyano-pindolols, propanolols, alprenolols, etc... Reference may also be made to the monograph edited by A. D. Strosberg, in which many other agonists and antagonists of membrane receptors corresponding to the definitions of the invention are identified.

In one of these preferred applications, the invention thus relates to cell cultures composed of unicellular cells especially bacteria, containing vectors which can replicate within these organisms, these vectors meeting the conditions indicated above and containing an insert coding for a mammalian membrane receptor in compliance with the definitions indicated above, the expression of these inserts being inducible or, having been induced, leading to the transport of the corresponding membrane receptors to the membrane, depending on the nature of the promoter used.

In a preferred embodiment of the invention, the modified vector is characterized in that the insert codes for a sequence of amino acids contained in a mammalian receptor of the kind indicated above containing in its structure hydrophobic transmembrane segments inserted between extra- and intra-cellular loops, a carboxyl-terminal intra-cellular segment and an amino-terminal extracellular segment and binding sites constituted by hydrophilic regions formed in the membrane.

For the construction of the vector according to the invention, an inducible promoter is advantageously used. Such a promoter can be regulated and is only functional after induction by a biochemical molecule or by a physical treatment (treatment by temperature, ultraviolet rays, etc.). The use of such an inducible promoter enables the nucleotide sequence contained in the vector to be expressed only under conditions specified beforehand by the investigator. In this manner, damage to the cells of the transformed host culture by the modified vector is avoided, each time that the foreign receptor is to be expressed in the cell and transported into the membrane the host cell is exposed to a certain degree of toxicity.

In accordance with another embodiment of the vector according to the invention, the insert coding for the receptor can be placed downstream from a "leader sequence" or "signal sequence" and in phase with the latter, in order to form a transcription unit, this "leader" sequence thus being able to facilitate the transport of the product of expression of the insert to the membrane of the unicellular host. This "leader" sequence usually codes for a N-terminal sequence of a precursor of a protein of the unicellular host normally transported to the membrane of the cell, this N-terminal peptide normally being cleaved when the corresponding natural protein has been transported to the membrane of the unicellular host. Similarly, the fusion gene between this "leader" or signal sequence and the insert should normally be expressed in the form of a hybrid protein cleaved downstream from the signal sequence when the receptor has been transported to the membrane of the unicellular host.

As an alternative, the insert is fused to a sequence coding for all or a part of a hydrophilic protein (for example β-galactosidase), this fusion insuring that the hybrid protein, the product of the expression of the insert and the sequence coding for the hydrophilic protein, remains soluble during the transport of the receptor resulting from the expression of the insert in the unicellular host into the membrane of this latter.

The invention also relates to unicellular organisms themselves transformed by a modified vector such as that described above, and more particularly to cultures of unicellular organisms carrying on their surface sites or determinants recognized by specific ligands for the corresponding mammalian membrane receptors.

In order to implement the invention and obtain the expression of the nucleotide sequence corresponding to the selected protein, use should preferably be made of a unicellular organism selected from among bacteria, yeasts or any other unicellular organism which can accept the modified vector according to the invention and allow both its replication as well as the expression of the selected protein and its transport to the surface of the cell.

The invention also relates to a procedure for the production of unicellular organisms containing, exposed at their surface, sites characteristic of a mammalian membrane receptor, this procedure being characterized in that it comprises:

a/ the transformation of a unicellular organism by a vector which can replicate in this organism, modified beforehand so that it contains a promoter recognized by the polymerases of the unicellular host and functional in the latter and an insert placed under the control of this promoter and coding for a sequence of amino acids usually contained in a mammalian membrane receptor such as that described above.

b/ the selection of transformed unicellular organisms in which the above-mentioned insert is expressed or can be expressed in a form such that its structure comprises one or more sites exposed at the exterior of the cell membranes and is capable of being recognized by a corresponding ligand. As an alternative, the detection of expression can be performed by having recourse to specific antibodies, in particular monoclonal antibodies, which specifically recognize these same sites.

When the unicellular organism is transformed by a modified vector containing an inducible promoter upstream from the nucleotide sequence to be expressed, a step intermediate between the steps a/ and b/ cited earlier is necessary, this step consisting of the induction of the said promoter, in particular as a result of the action of a suitable substance (for example IPTG (isopropyl-D-thiogalactopyranoside) in the case of the promoter of the lactose operon and tryptophan and in the case of the promoter of the tryptophan operon) added to the culture medium when induction is desired.

The present invention also relates to a procedure for the detection of the capacity of a molecule to behave as a ligand for a membrane receptor, this procedure comprising:

a/ the placing in contact of the molecule with a unicellular organism previously transformed by a vector, itself modified by an insert coding for this membrane receptor, this organism carrying on its surface one or more specific sites of this receptor, where appropriate after induction of the expression of this insert, the placing in contact being performed under conditions leading to the formation of a bond between at least one of these specific sites and the molecule provided that it has been shown actually to possess an affinity for this receptor.

b/ the detection of the possible formation of a complex of the ligand-receptor type.

The conditions making possible the formation of the above-mentioned bond usually correspond to those conditions under which such bonds are formed between natural receptors and the ligands concerned.

The invention also relates to a procedure for studying the affinity of a mammalian receptor belonging to the class of those which are coupled to a G protein for one or more defined ligands, characterized by:

the transformation of a unicellular culture with a vector, in particular a plasmid or a phage into which has previously been incorporated a sequence of nucleotides coding for the polypeptide contained in this mammalian receptor under the control of regulatory elements, in particular a promoter, making possible the expression of the said nucleotide sequence in the unicellular culture used:

the culture of the transformed unicellular organisms under conditions which permit the expression of the insert, the placing in contact of these unicellular organisms with specific ligands, the detection of a specific affinity reaction between the transformed unicellular organism and the specific ligands.

The invention also relates to a kit for the detection of the possible affinity of a ligand for a specific mammalian membrane receptor, comprising;

a culture of unicellular organisms transformed by modified vector such as that described in the preceding pages in which the insert codes for an above-mentioned membrane receptor, physical or chemical agents to induce the expression of the nucleotide sequence contained in the modified vector when the promoter placed upstream from this sequence is a promoter inducible by these physical or chemical agents, one or more control ligands having defined affinities for the membrane receptor, chemical or physical agents for the characterization of the biological activity of the protein.

The invention thus furnishes agents which also make possible the study of the behavior of functional proteins as receptors as a consequence of the exposure of their specific sites at the surface of unicellular organisms when the latter have been subjected to prior transformation by vectors containing an insert coding for the said functional protein. The invention also makes possible the detection or verification of the affinity of a protein as a receptor for a specific ligand. It also makes possible the study of the specificity of bonding of these receptors to different ligands selected for their importance, for example as regards future types of therapy.

A particular advantage of the invention lies in the substitution of the receptors, the purification of which is extremely difficult and the time of storage minimal, by cells expressing, or capable of expressing at their surfaces the sites characteristic of receptors which can be recognized by the ligands under study. These cells can be stored easily, particularly when the modified vector comprises a promoter which can be induced when it is required. Owing to their capacity to be cultivated, the cells enable the specific sites of these receptors to be regenerated in almost unlimited quantities on demand.

The cultures of unicellular organisms transformed by a modified vector previously described can be stored until they are required for use by placing them in particular in a 20% final glycerol solution at −70° C. They may also be stored in the form of spores.

The invention lends itself to many applications. Some of them will be mentioned below, as examples.

Particularly interesting applications in the areas of therapy consist of the study of the capacity of novel β-blocking substances capable of acting at the level of the β-adrenergic receptors, in particular β1-adrenergic (in the heart) or β2-adrenergic (in the lung) receptors.

It has been observed that many so-called β-blocking substances bind to both β1 and β2-adrenergic receptors. Certain types of therapy require, however, the use of medicines specific for one or other of these receptors and thus implies the determination of subtypes of receptors capable of binding to specific ligands. The invention makes it possible to prepare unicellular cultures capable of facilitating the screening of ligands according to the types of activities shown for different types of β-adrenergic receptors: it thus makes it easy to determine the pharmacological and therapeutic specificities of medicines under study.

The invention also provides simple agents for the study of the effects of modifications introduced into the receptors with respect to their interactions with chemical substances, in particular with ligands known for their ability to bind to these receptors in their unmodified forms.

Other properties and advantages of the invention will become apparent in the description which follows and in the examples, and in particular in relation to the drawings and the table in which:

Table 1 presents the results recorded with β-adrenergic ligands binding the hu-β2 receptor expressed in intact *E. coli* cells and their behavior in the presence of agonists and competitive antagonists.

Figure 1:
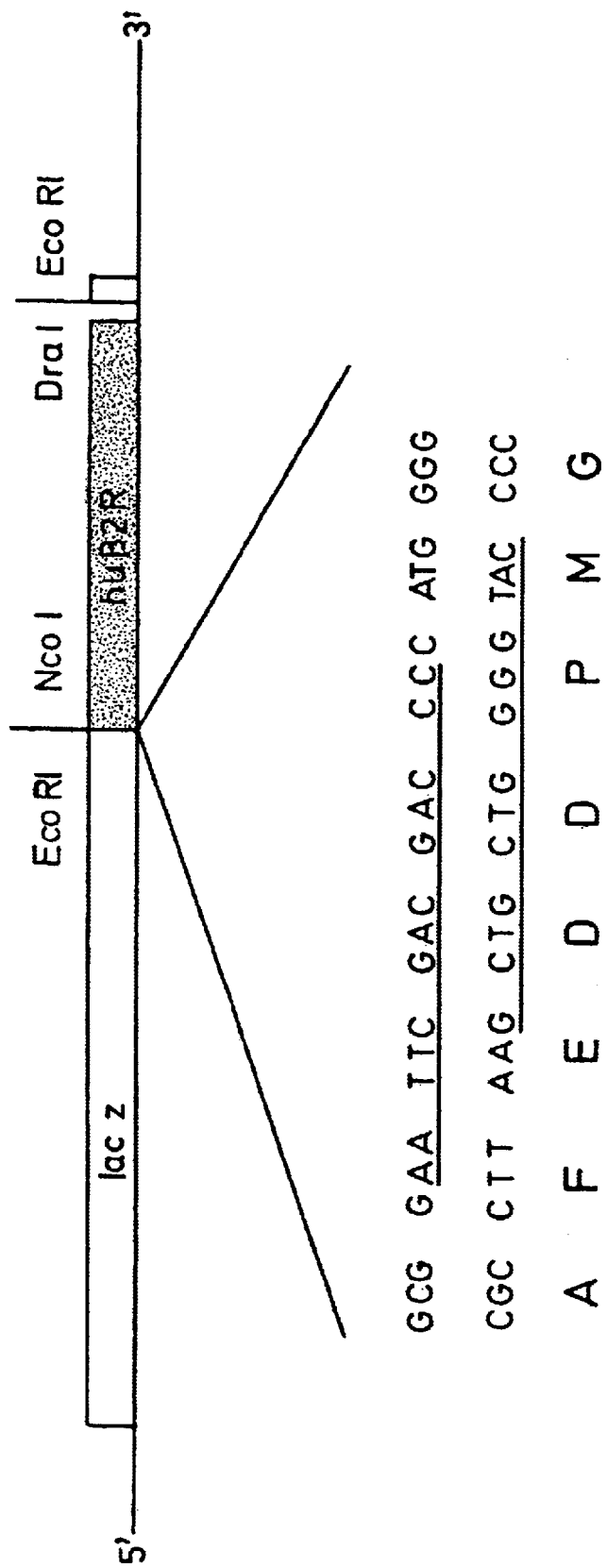
FIG. 1 presents a schematic representation of the regions coding for the human β2-adrenergic receptor (hu-β2 R) recombined with the β-galactosidase gene (lac Z) of the phage λgt11(11).

FIG. 1 shows the restriction sites used for the construction of the fusion gene. The initiation codon for the hu-β2R gene is included in the NcoI restriction site and its termination codon is located 19 base pairs upstream towards the 5' end of the Dra I restriction site.

Figure 4:
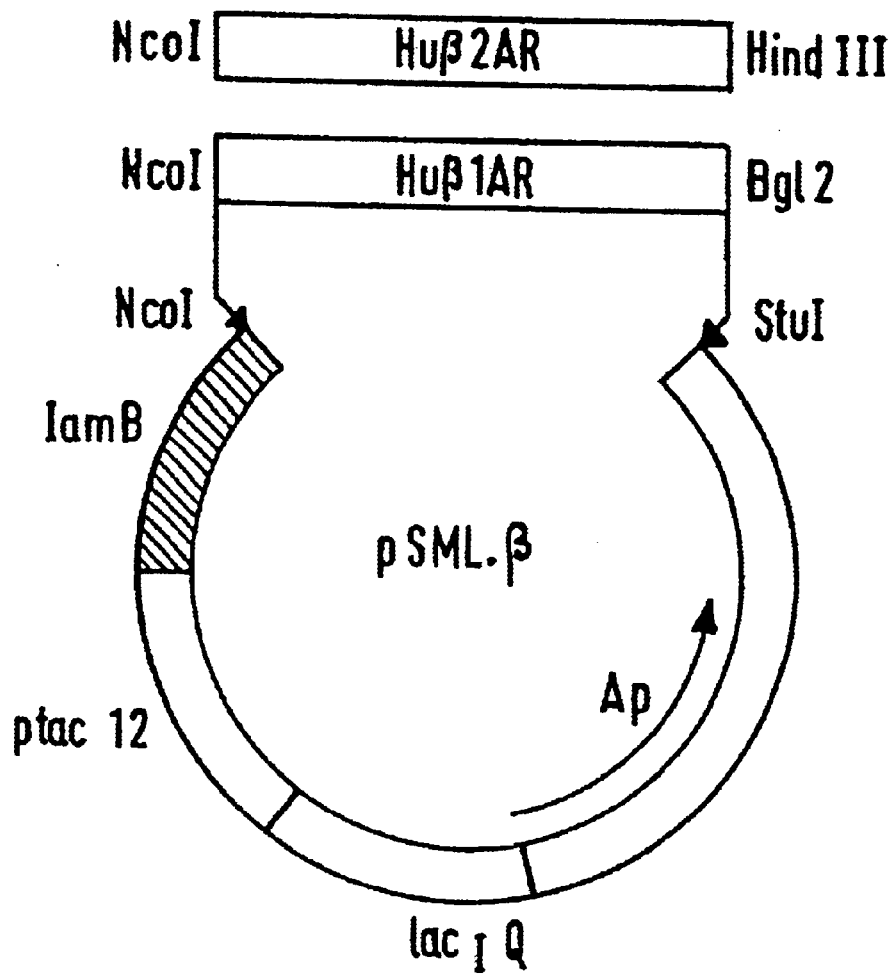

In the lower part of this figure, at the junction between the two genes, the linker which extends from the EcoRI site to the NcoI site and which maintains the reading frame of the lacz gene in phase with that of the hu-β2R gene is underlined. The corresponding sequence of amino acids is represented beneath the nucleotide sequence by using the following code for the designation of the amino acids:

M Methionine
L Leucine
I Isoleucine
V Valine
F Phenylalanine
S Serine
P Proline
T Threonine
A Alanine
Y Tyrosine
H Histidine
Q Glutamine
N Asparagine
K Lysine
D Aspartic Acid
E Glutamic Acid
C Cysteine
W Tryptophan
R Arginine
G Glycine Legend of the New Drawings FIG. 4 represents the construction of plasmids pSMLβ1 and pSMLβ2

FIG. 5

A. Saturation curves and a scatchard representation (inset) of ICYP binding to intact bacteria expressing Huβ1AR or Huβ2AR. Results are the mean of two independent experiments performed on the same bacterial culture and are representative of four different preparations. One class of binding sites is present for each receptor. Calculated $K_D$ were 16,40±0.45 pM for Huβ1AR and 17,00±0.36 pM for Huβ2AR.

B and C. Inhibition binding experiments performed on Huβ1AR(B) and on Huβ2AR(C) expressed by intact *E.coli* (−)Epinephrine (△)(+) Norepinephrine (▲), (−) propranolol (□), (+) propranolol (■), CGTP20712-A (●), ICI118,551 (○) were used to displace 10 pM ICYP.

FIG. 6

Photoaffinity labelling of Huβ1AR(lanes b and c) and Huβ2AR(lanes a) on intact *E.coli*. Experiments were performed in the presence (underlined letters) or in the absence of cold propranolol in order to show the specific binding. Arrows indicate the expected molecular weight of HuβARS separated from the LamB polypeptide.

FIG. 7

Schematic representation of the procedure proposed for the screening of ligands interacting with β-adrenergic receptors.

EXAMPLE 1
Expression of the Human β2-adrenergic receptor in *E. coli*
1/ Construction of the Recombinant Gene This step involves the insertion of the coding region for the human β2-adrenergic receptor into the expression vector λgt11 at the EcoRI restriction site, close to the 3' end of the lac Z gene coding for β-galactosidase.

In a first step, the linker extending from the EcoRI site to the NcoI site is joined to the purified DNA fragment of 1.3 kD extending from the NcoI site to the DraI site which contained the coding region for the human β2-adrenergic receptor.

This linker contains a sequence coding for the sequence of amino acids Asp-Asp-Pro and will facilitate the separation of the fusion protein obtained after the subsequent step of expression of the recombinant gene by hydrolysis of the Asp-Pro bond by means of a mild acid cleavage.

After extraction with phenol and precipitation with isopropanol, EcoRI linkers were joined to this construction which, after digestion with EcoRI and purification, was inserted at the unique EcoRI site in the vector λgt11. A control was carried out to verify that the EcoRI and NcoI sites as well as the orientation of the inserted gene had been preserved.

The recombinant fragment (or recombinant gene) obtained between the fragment derived from the lac Z gene and the hu-β2R fragment by the intermediary of the linker are shown in FIG. 1. The figure also shows the 3' and 5' end of the DNA of λgt11 as linear extensions on either side of the recombination fragment.

2/ Expression of the Recombinant Gene in *E. coli*

The recombinant vector obtained was inserted into the *E. coli* strain Y1089 by lysogenization of this latter with the recombinant phage by a standard technique, described in detail in reference (11). The cells were then harvested and resuspended in a 10 mM tris buffer, pH 7.4, containing 90 mM NaCl. The expression of the fusion protein can be produced after induction of the promoter by thermal shock and by placing the transformed cells in contact with isopropyl β-D-thiogalactopyranoside (IPTG). An analysis of the bacterial lysate by an immunoblot test in the presence of anti-β-galactosidase antibodies showed the presence of products varying between 100 and 162 kDa in size.

3/ Study of the Activity of the Receptors Thus Expressed at the Surface of *E. coli*, with Ligands Capable of Forming Bonds of the Receptor-Ligand Type In order to carry out this study, several β-adrenergic ligands are used as well as negative controls comprising, for example, the *E. coli* bacterium transfected with the expression vector lacking the nucleotide sequence coding for the β-adrenergic receptor, or also this vector containing the above-mentioned sequence inserted in the sense opposite to that of the reading frame. *E. coli* Y1089 cells expressing the hybrid gene in the form of a fusion protein are suspended in a solution of 10 mM Tris, pH 7.4, containing 90 mM NaCl. After induction of the expression of the receptor, aliquots containing 6×10⁷ cells are then incubated for 1 hour at 37° C. in a final volume of 1 ml of ICYP ([$^{125}$I] iodocyanopindolol, 2080 Ci/mmol, from the AMERSHAN Laboratories) at different concentrations (1 to 80 pM).

The reactions are stopped by filtration through WHATMAN GF-F filters, followed by 4 rapid washings with 4 ml of buffer. The existence of non-specific binding is determined in the presence of 1 mM of propanolol; such binding is less than 23%.

Figure 2:
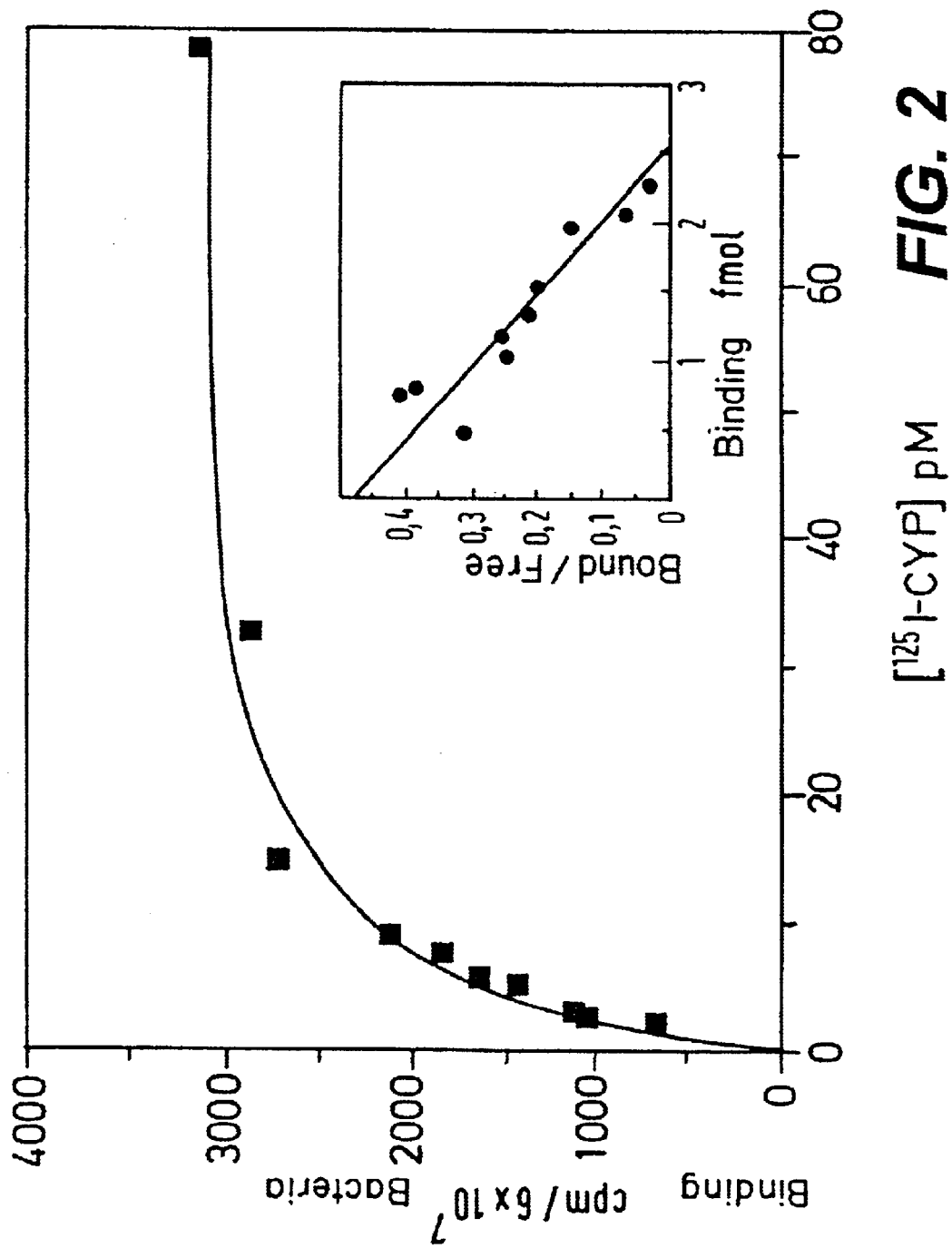
FIG. 2 shows the variations in the affinity of binding between the molecules of a ligand, ICYP and intact cells of *E. coli* expressing the hu-β2R sequence of FIG. 1 contained in the fusion gene.

FIG. 2 presents the curve shoving the variation of the proportion of ligand bound by 6×10⁷ bacteria as a function of the concentration of ligand (ICYP) (from 1 to 80 pm of [$^{125}$] ICYP). This curve is a saturation curve; it corresponds to a unique class of binding sites characterized by a Kd of 5.3±1.9×10⁻¹² M (r=0.93). Calculation shows that the maximal number of sites permitting binding of the receptor to the ligand is 25.5±5.2 per bacterium.

Similar experiments carried out with bacteria infected with the wild-type λgt11 vector (lacking the gene for the human β2 receptor) or with bacteria infected by a phage containing the gene for this receptor inserted in the opposite sense shoved that less than 0.5% of binding was measured.

It was observed that the expression of the human β2-adrenergic receptor is maximal after 2 hours of induction and stable for up to 20 hours. This corresponds to the maximal bacterial density; this observation suggests that there exists an inhibitory effect of the product expressed by the gene inserted into the expression vector on bacterial growth.

Figure 3:
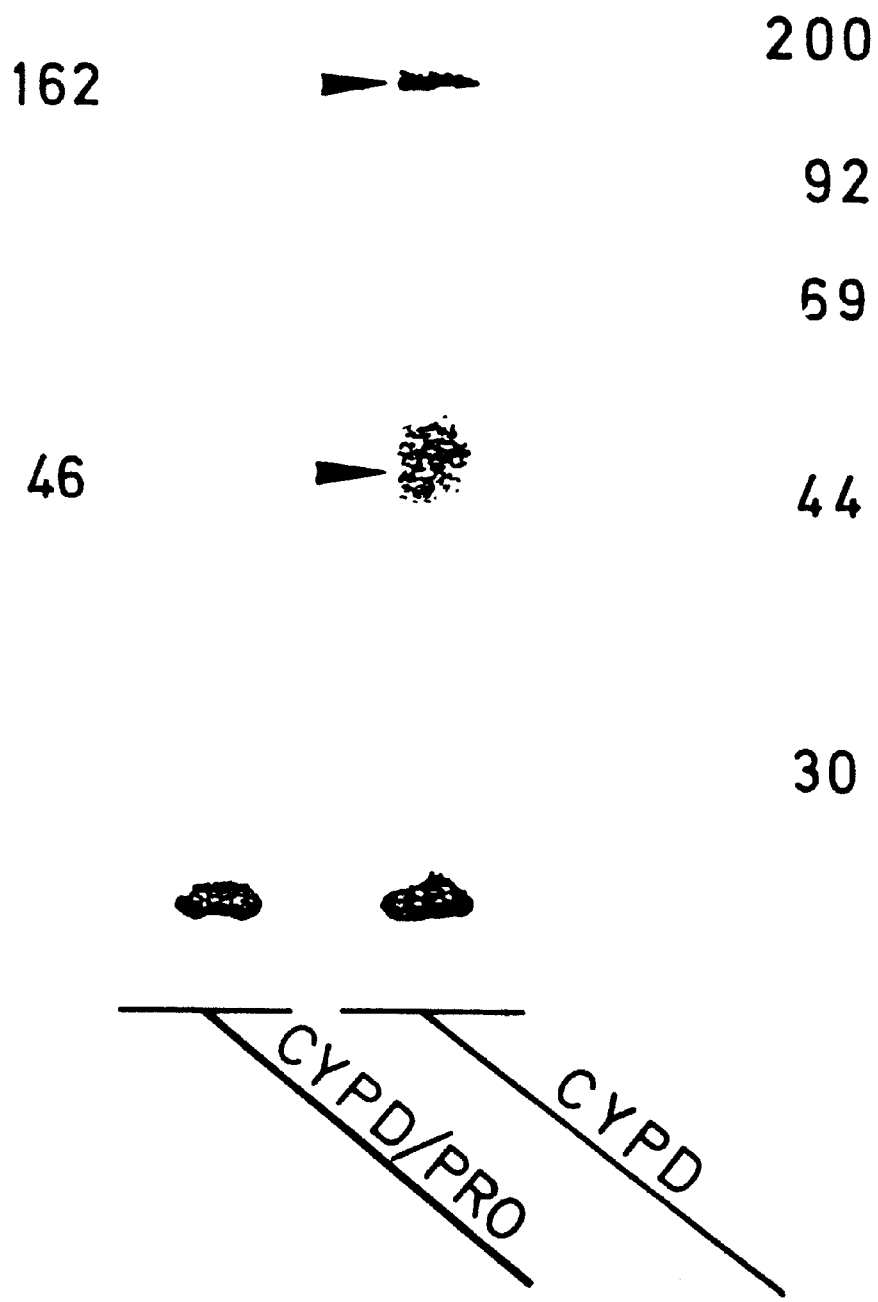
FIG. 3 illustrates the expression of β2-adrenergic receptors expressed in the membrane of *E. coli* detected by the aid of photo-affinity labelling.

The ligand can be displaced from its binding site by distinct ligands capable of competing with the former (see, for example, the complete displacement of the ICYP ligand by the hydrophilic ligand CGP 12177 in the assays described further on in reference to the table. After separation of the cytoplasm, the activity remains associated with the membranes (see discussion of FIG. 3).

The non-induced intact cells can be stored in a mixture of 10 mM Tris, 90 mM NaCl at pH 7.4 for at least 3 days at 4° C. without loss of binding activity for the ligand.

4/ Photo-Affinity Labelling of the β2-Adrenergic Receptor Expressed in the Membrane of *E. coli*

Bacteria prepared according to a protocol similar to the one described in the preceding step are resuspended in a volume corresponding to 1/20 of the volume of the original culture in a buffer containing 10 mM Tris, pH 7.4, 150 mM NaCl, 0.5 mM of phenylmethyl-sulfonyl fluoride, 2 mM EDTA, 5 µg per ml of leupeptin, 7 µg per ml of pepstatin, 10,000 U per ml of trasylol and 4 µg per ml of benzamidine. This buffer will also be used in all subsequent steps.

The cells are then frozen (in liquid nitrogen) and thawed 4 times to obtain complete lysis. The DNA is then disrupted by sonication (3 periods of 10 seconds at 10 watts) in order to reduce the viscosity, and the lysate is centrifuged for 20 minutes at 6,000 g in order to remove the cell debris and the intact cells.

The supernatant was then centrifuged for 2 hours at 100,000 g. The pellet from the centrifugation was resuspended in 4 ml of buffer, homogenized in a glass recipient, and the binding activity was measured with ICYP on both the pellet and the supernatant fractions.

The activity associated with the cytoplasmic proteins was 0% (determined by precipitation in 12% of polyethylene glycol 6,000) whereas 26.6% of the initial binding activity was found in the membrane fraction.

For photo-affinity labelling, about 200 fmoles of sites capable of binding to ICYP were incubated in 1 ml in the dark for 1 hour with 500 pM of ICYP-D (Iodo-Cyano-Pendolol-Diazirine) (AMERSHAM 1800 Ci/mmol) at 37° C. in the presence or absence of 5 µM (−) propanolol. 4 ml of buffer were added and the membranes were washed 3 times by centrifugation (15 minutes at 45,000 g) and resuspended. Photolysis was carried out under conditions previously described (15). The labelled membranes were solubilized in Laemmli buffer (16) containing 5% SDS, then subjected to electrophoresis in a 10% polyacrylamide gel and autoradiographed.

These results show that the receptor activity is concentrated essentially in the membranes as is confirmed by identification of the fusion products located at 162 kDa and the free receptor (46 kDa).

The data presented in the table are obtained from competition binding experiments carried out with bacteria such as those referred to in FIG. 2 by using 20 pM of ICYP as radioactively labelled ligand, and various concentrations of different ligands capable of competing with the former. The analysis of the competitive effects of the ligands on the binding curves of the ligand ICYP to the cells and the determination of the $IC_{50}$ values were made by using a computer program adapted to the assays in the context of simple competition experiments (12).

Each substance studied in the competition experiments was tested 2 to 4 times in separate experiments. The $K_i$ values were calculated from the $IC_{50}$ values, as is reported in (14).

The stereoisomers are indicated by (+) or (−).

The pharmacological profiles resulting from the possibilities of displacement or not of the bound ligand (ICYP) by other substances prove to be of the same type as those which characterize the same receptors in their normal cell hosts (mammals).

However, contrary to what is observed in the normal host cell, no associated coupling or interaction is observed between the human β2-adrenergic receptor and the adenylate cyclase, in particular when the active ligands, in particular isoproterenol, are placed in contact with the transformed cells, and this is so although *E. coli* contains the elongation factor Tu which is itself a G protein capable of controlling the synthesis of proteins (17) and of acting as a regulator of adenylate-cyclase activity. This apparent lack of coupling is perhaps due to differences between the G proteins of bacteria and the G proteins of mammals.

A strain of the cell culture of *E. coli* transformed by a vector modified according to the invention by the hu-β2-adrenergic gene and designated as HU-β2-Coli has been deposited with the National Collection of Culture of Microorganisms of the Pasteur Institute at Paris (CNCM) under the number I-737 on Mar. 3, 1988.

TABLE 1

| Compound | Pharmacological property | $K_i$ (nM) |
|---|---|---|
| (−) norepinephrine | agonist | 9100 ± 1100 |
| (−) epinephrine | agonist | 4700 ± 1400 |
| (+) isoproterenol | agonist | 1400 ± 100 |
| (−) isoproterenol | agonist | 110 ± 10 |
| procaterol | agonist β2 | 40 ± 8 |
| CGP 20712-A | antagonist β1 | 2500 ± 600 |
| practolol | antagonist β1 | 790 ± 220 |
| CGP 12.177 | antagonist | 4.8 ± 1.3 |

EXAMPLE 2

Expression in *E.coli* of the β1 and β2 Human Adrenergic Receptors

Expression in *E.coli* of the β1 and β2 human adrenergic receptors (designated by Huβ1AR and Huβ2AR) using, as vector, a plasmid in which the coding region of the receptors" genes is fused in phase with the 5' extremity of the LamB gene (23) has been realized. Stable clones of transformed bacteria, producing pharmacologically active receptors, have been obtained. The pharmacological profile of each receptor expressed in *E.coli* is analogous to that observed in reference mammalian tissues. This new expression system constitutes a particularly advantageous system according to the invention. Bacterial clones expressing one type of human β-adrenergic receptors constitute accordingly an appropriate tool for the rapid screening of new synthetic molecules.

Experimental Procedure
Bacterial Strains and Plasmids

JM 101 (25) and pop 6510 (24) *E.coli* strains we respectively the recipients for transformation with pUC 19 (25) and AJC-264 derived plasmids.

The cloning and sequencing of Huβ2AR gene was described previously (3). The Huβ1AR gene was selected from a human placental library in EMBL 4 using as probe the coding region of the gene for the turkey β-adrenergic receptor [Yarden et al PNAS 83 P6795–6799(1986)]. The restriction map of the Huβ1AR was identical to that reported in the literature (1). The coding regions of Huβ2AR and Huβ1AR were first subcloned in the EcoR1 site of pUC 19. A NcoI restriction site, naturally present in the Huβ2AR gene, was created at the level of the first codon in Huβ1AR gene. This step was achieved by removing the 5' of the coding region and replacing it with synthetic oligonucleotides that reconstituted an equivalent codon sequence. The structures of these constructs were assayed by restriction analysis.

The plasmids pSMLβ1 and pSMLβ2, carrying the LamB-HuβAR hybrid genes, were derived from the multicopy plasmid AJC-264 (24). The AJC-264 plasmid encodes the LamB gene under the control of ptac 12 promoter (23). LamB codes for an *E.coli* outer membrane protein involved in the permeability of maltose and maltotriose. This plasmid also contains a 1.1 Kb portion comprising the lac$I^Q$ gene and its promoter. The expression of LamB is therefore repressed to a basal level of 1.500 monomers. Upon induction by $10^{-3}$ M IPTG a 30–40 fold increase of LamB expression is achieved (23).

The AJC-264 plasmid was cut by NcoI and StuI: the NcoI site corresponds to amino acid 279 of mature LamB protein, and StuI site is situated 82 base pairs following the last codon of LamB. The NcoI-HindIII fragment of Huβ2AR and the NcoI-Bgl2 fragment of Huβ1AR were subcloned in the NcoI-StuI sites of pAJC-264. In these constructs the same reading frame was maintained between the LamB portion and the HuβARs. Purification of DNA fragments was carried by migration in 0.8% low melting agarose (LMP Agarose, Pharmacie); ligations were performed directly in the gel following the procedure described in (26). The *E. coli* strain pop 6510 was transformed with the recombinant plasmids according to standard techniques (26).

Media and Culture Conditions

Recombinant and control *E.coli* strains were cultivated in Luria broth (L-broth) (1% tryptone, 1% NaCl, 0.5% yeast extract, pH, adjusted to 7) or L-agar solid medium (L-broth solidified with 1.5% bactoagar DIFCO) containing 100 μg/ml sodium ampicillin (Sigma, St.Louis USA).

For standard preparations, 50 ml of broth were inoculated with a single colony grown overnight on L-agar solid plates and incubated at 37° C. with vigourous aeration. Once the optical density measured at 600 nm reached 0.4–0.6, 0.1 mM final IPTG (Sigma, St.Louis USA) was added and the cultures were grown at 23° C. for 4 hours. For larger preparation up to 1 liter the same general procedure was followed, excepting that the medium was inoculated with a suspension of bacteria in exponential growth phase, in order to start the culture at 0.05 $OD_{600\ nm}$. Bacteria were finally centrifuged at 1500 g, resuspended in NaCl 100 mM, Tris 10 mM pH 7.4 buffer and strored at 4° C.

Binding Assays

Aliquots containing $6 \times 10^7$ cells were incubated for 1 h at 37° C. in a final volume of 1 ml with ICYP ($[^{125}I]$ iodocyanopindolol, 2080 Ci/mmol, Amersham, UK) at various concentrations (from 1 to 80 pM). Reactions were stopped by filtration on Whatman GF-F filters followed by four rapid washes with 4 ml of buffer. Non-specific binding, determined in the presence of 1 μM(-)propranolol was less than 25%. No saturable binding could be measured on control *E.coli*, transfected with AJC-264 plasmid. Competition binding experiments were performed as in direct binding assays using 10 pM ICYP as radiolabeled ligand and various concentrations of competitors. Each drug completely inhibited the ICYP binding to the receptor. A computer program for simple competition (11) was used for analysis of the curves and for determination of $IC_{50}$ values. $K_i$ values were calculated from $IC_{50}$ values as reported (12).

Photoaffinity Labeling

Photoaffinity labeling was carried out on cells suspension in 10 mM Tris, pH 7.5, 100 mM NaCl. Each reaction mixture of 1 ml, containing 500 pM$[^{125}I]$ iodocyanopindolol-diazirine (CYPD, Amersham 1800 Ci/mmole) and about 100–200 pM of ICYP binding sites, was incubated for 1 h at 37° C. in the absence or presence of 5 μM(-)propranolol. Five ml of 10 mM Tris, pH 7.5 were then added and the cells were centrifuged at 5,000×g for 10 min. Following suspension in 10 ml of the same buffer, photolysis was performed and cells were washed as described (15). Labeled bacteria were solubilized in Laemmli sample buffer containing 10%NaDodSO4, incubated for 2 h at room temperature, subjected to electrophoresis in 10% polyacrylamide gels in the presence of $NaDodSO_4$ (16) and autoradiographed.

Results

Figure 5A:
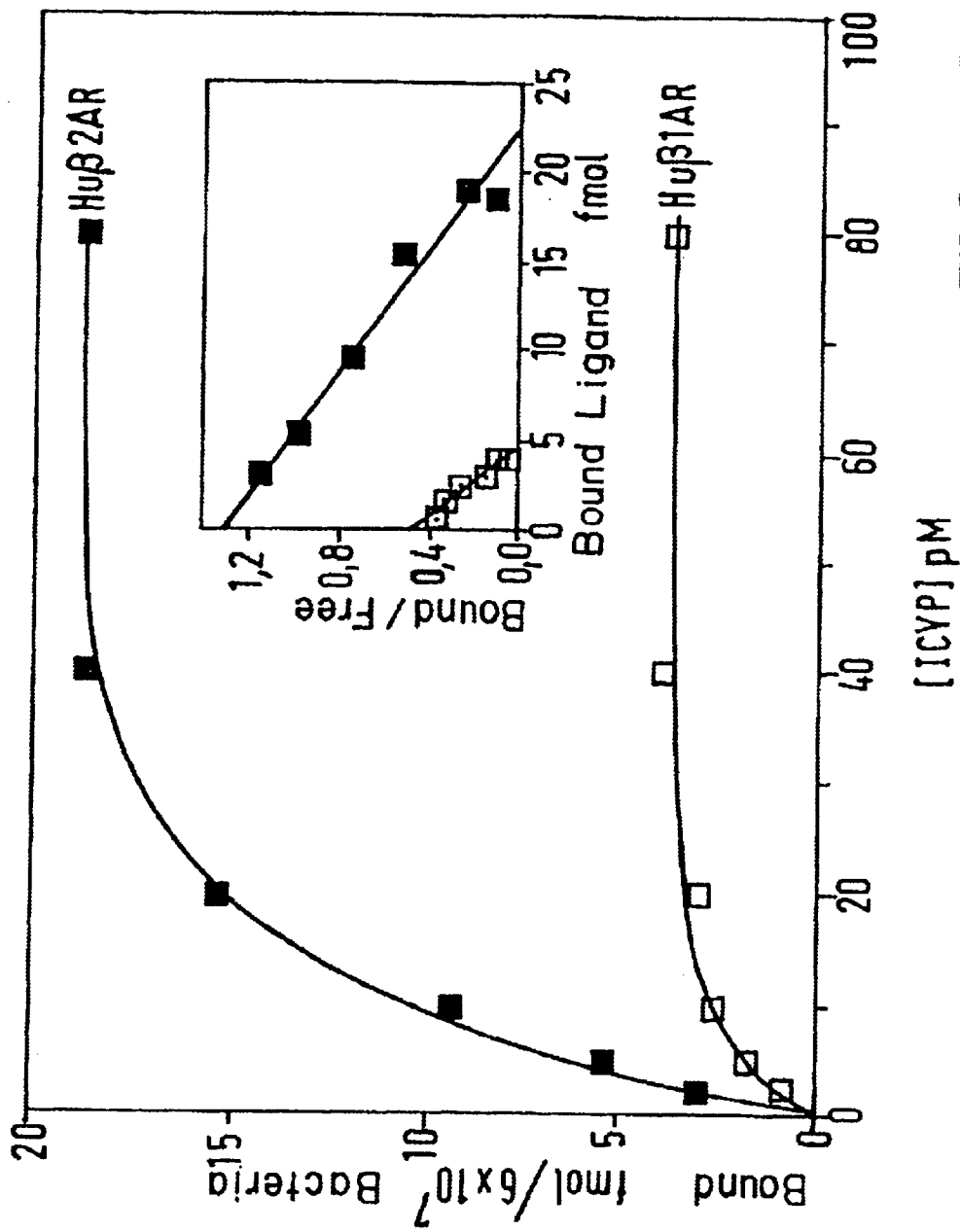
Figure 5B:
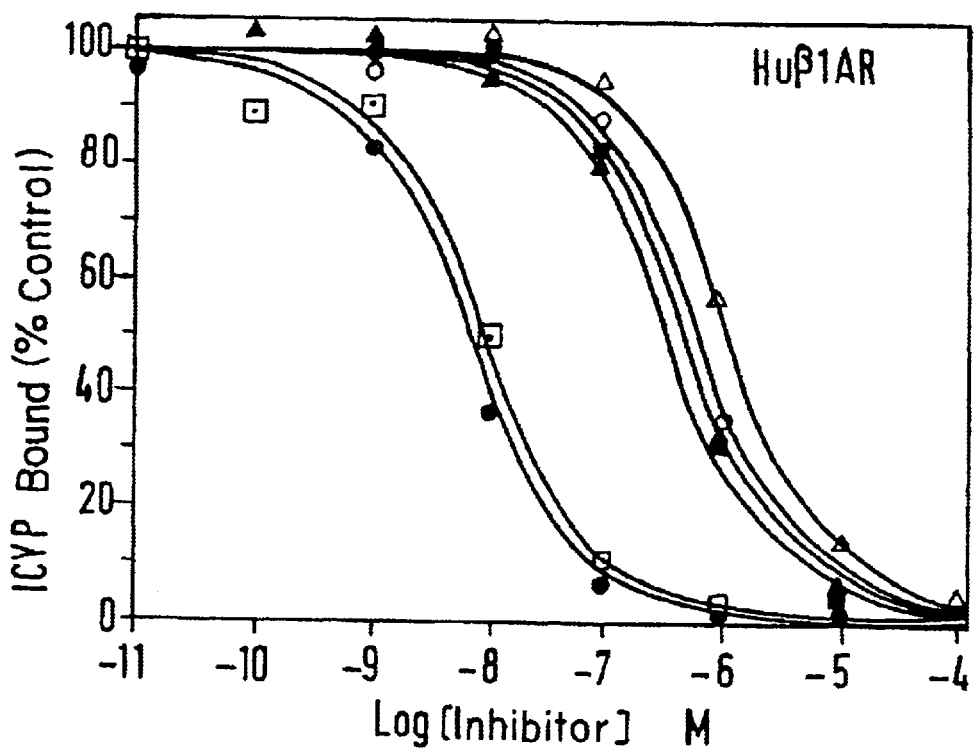
Figure 5C:
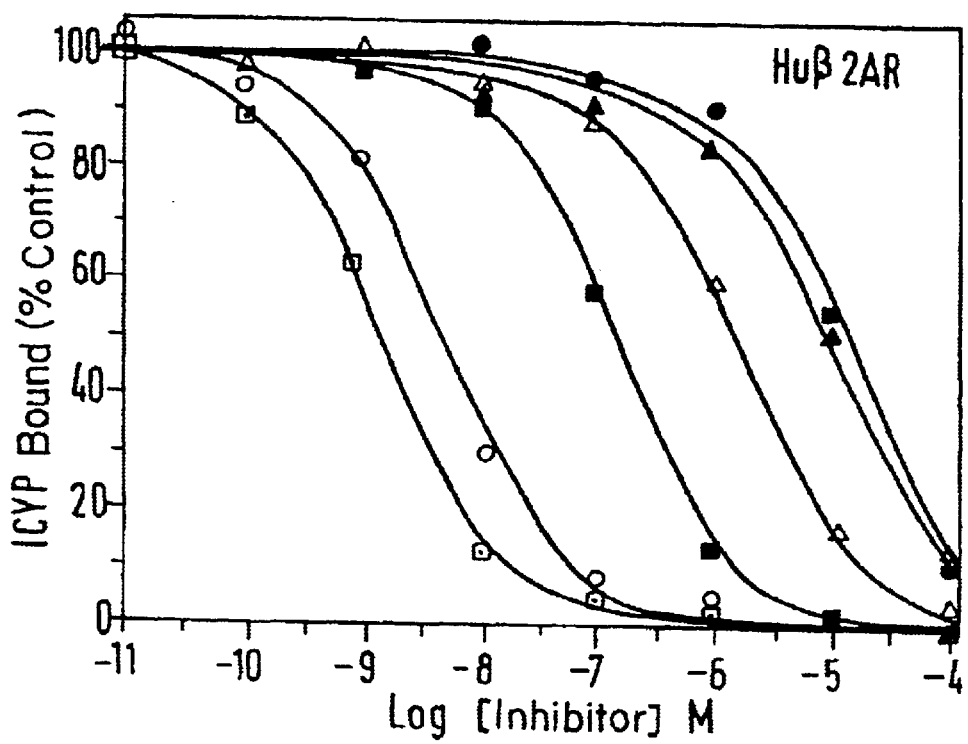

The coding regions of Huβ1AR and Huβ2AR were fused in phase to the 5' part of the lamB gene (coding for the first 279 amino acids of the LamB protein), carried on the multicopy plasmid AJC-264(24) under ptac 12 promotor control. *E.coli* K12 pop 6510 strain, were transfected with the resulting plasmids, respectively called pSMLβ1 and pSMLβ2 (FIG. 4). Stable clones were obtained, which expressed saturable binding sites for the β-adrenergic antagonist $^{131}$I-iodocyanopindolol (ICYP) upon IPTG induction (FIG. 5). As shown in competition binding assays (FIG. 5), *E.coli* transfected with pSMLβ1 expressed β-adrenergic receptors of β1 pharmacological class, while pSMLβ2-containing bacteria produced adrenergic receptors of the β2 subtype. Both β1 and β2-adrenergic receptors displayed the expected stereospecificity, since the levorotatory form of propranolol bound to the receptors with higher affinity than its dextrorotatory counterpart.

About 220 Huβ2AR receptors were expressed per bacteria. The number of active β1 receptors was repeatedly found to be around 50 per bacteria. This lower expression level could probably be improved by diminishing the high sensitivity of the expressed protein to bacterial proteases.

Figure 6:
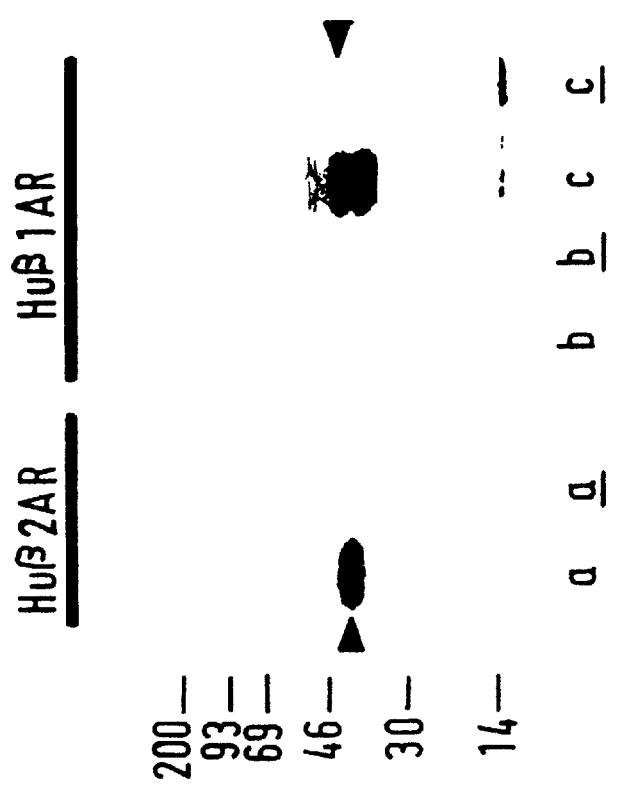

In order to visualize the two receptors at the molecular level, photo-affinity labelling experiments were performed on intact bacteria, using as photoactivable ligand, the diazirine derivative of ICYP (FIG. 6). The expected molecular weight of the fusion LamB-Huβ1AR and LamB-Huβ2AR proteins are respectively 83 and 72 KDa. Neither of these is labelled by the photoactivable ligand. For the β2 receptor the majority of labelled molecules was under the form of a protein of 43 kDa, corresponding to the theoretical molecular weight of the receptor cleaved from its fusion partner. As expected less β1 than β2 receptors were labelled. When the experiment was repeated on a larger number of bacteria expressing β1 receptors, several molecular forms of active receptor were found ranging from 40 to 70 kDa, comprising free Huβ1AR (MW, around 47 kDa), fusion products cleaved in the LamB moiety (MW 43 up to 70 kDa and a major degradation form of Huβ1AR (MW of 40 kDa). This last form probably corresponds to proteolytic cleavage of the uHβ1AR moiety either at the N-terminus or at the C-terminus of the molecule, with conservation of the 7 putative transmembrane domains, that are necessary for a fully active receptor. Western blots carried out on membrane preparations of both β1- and β2-expressing bacteria with polyclonal anti-LamB antibodies showed that the fusion protein, which is not labelled by the photoactivable ligand, is on the contrary the major immunoreactive product.

Figure 7:
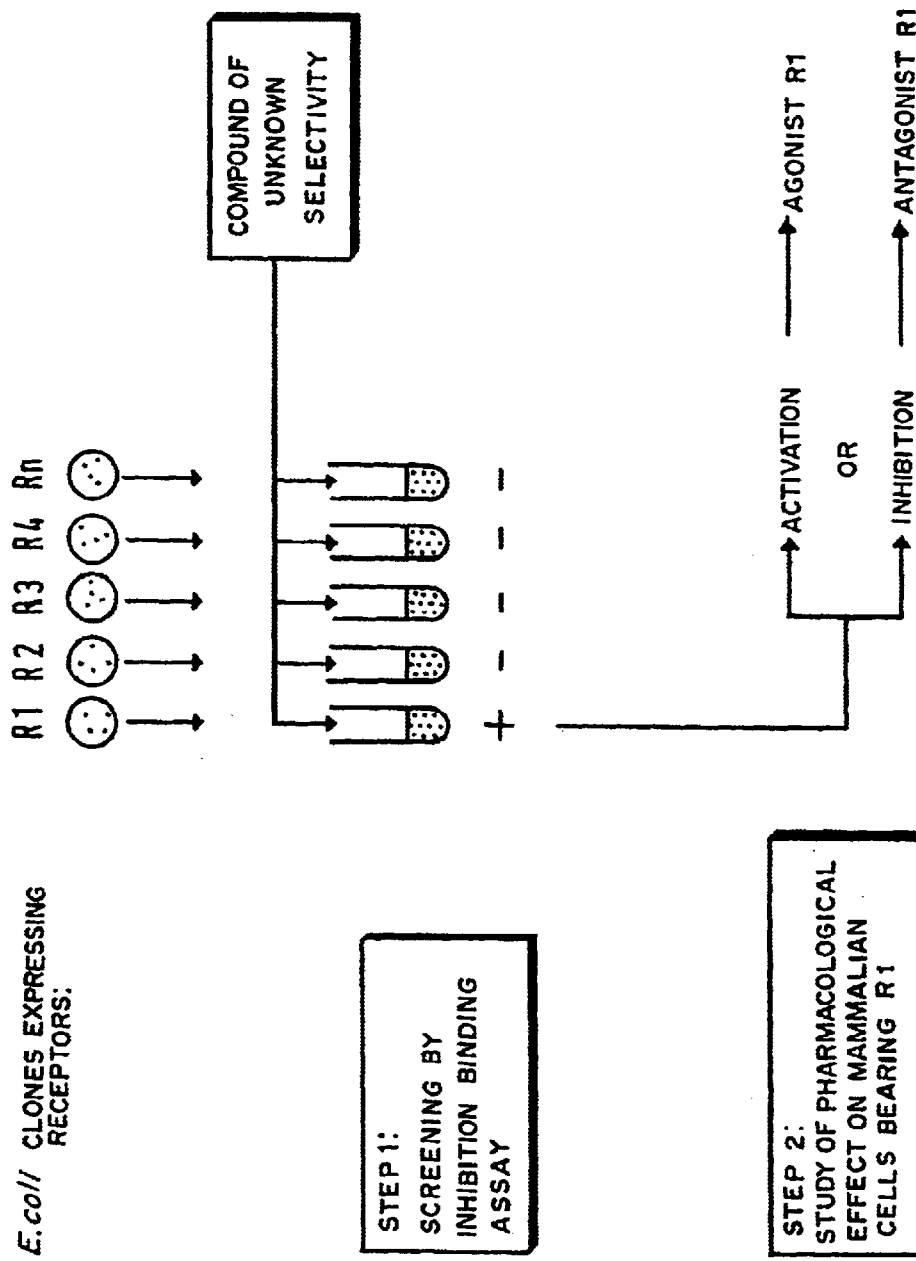

The number of active sites expressed by the bacteria is sufficient for the pharmacological studies of ligands which bind to β-adernergic receptors. With one liter of culture grown at 1.5 $OD_{600\ nm}$ about 20,000 assays may be performed, and IPTG induced bacteria can be stored in 15% glycerol at −70° C. for periods of at least 2 weeks without loss of more than 20% of their binding activity. A panel of compounds known to bind to mammalian β-adrenergic receptors was tested in competition binding assays on the 2 bacterial clones. As shown in Table 2, the calculated $K_i$ and the $K_i\beta1/K_i\beta2$ ratio are close to that determined for reference mammalian tissues. Therefore, the E. coli membrane environment, which differs from that of mammalian cells does not affect the fine binding properties of the receptors. Taken together, the pharmacological characteristics of β-adernergic receptors expressed in E.coli and the advantage of the bacterial culture compared to the time consuming and expensive procedures of receptor-enriched mammalian membranes, show that bacterial clones expressing membrane receptors constitute a tool for the screening of new synthetic compounds (FIG. 7).

The use of pSMLβ vectors represents a progress in terms of expression level of active receptors, when, compared to the system described in example 1 in which Huβ2AR was fused to β-galactosidase. This could be due to the properties of the LamB moiety, which is an E.coli outer membrane protein, by facilitating the correct folding of the fused receptors. Other bacterial polypeptides of different size and properties could be used as fusion partners for the expression of transmembrane receptors, and need to be tested systematically. The observation that photoaffinity labelled Huβ2AR correspond to native protein cleaved from the LamB peptide, prompted us to transfect bacteria with a similar plasmid in which the Huβ2AR gene was fused immediately 3' to the cleavage sequence of a becterial inner membrane protein signal peptide.

2. Dixon, R. A. F. et al. Nature 321, 75–79 (1986).
3. Emorine, L. Marullo, S. Delavier-Klutchko, C. Durieu-Trautmann, O. & Strosberg, A. D. Proc. Natl. Acad. Sci. USA. 84.6995–6999 (1987).
4. Kobilka, B. K., Matsui, H. Kobilka, T. S. Yang-Feng, T. L. Francke, U. Caron, M. G. Lefkowitz, R. J. & Regan, J. W. Science 238, 650–656(1987).
5. Kubo, T. et al. Nature 323, 411–416 (1986)
6. Bonner, T. I., Buckley, N. J. Young A. C. & Brann, M. R. Science 237, 527–532 (1987).
7. Masu, Y. Nakayama, K. Tamaki, H. Harada, Y. Kuno, M. & Nakanishi S. Nature 329, 836–838 (1987).
8. Spiegel, A. M. Mol. Cell. Edocrinol. 49, 1–16 (1987)
9. Engelman, D. M. Goldman, A. & Steitz, T. A. Meth.Enzym.88, 81–88 (1982).
10. Huynh, T. V. Young, R. A. & Davis R. W. in DNA Cloning, a Practical Approach Vol. 1, 49–78 (IRL, Oxford, 1985)
11. Minneman, K. P. Hegstrand, C. R. & Molinoff, P. B. Mol. Pharmacol. 16,34–46 (1979).
12. Cheng, Y. & Prusoff, W. H. Biochem. Pharmacol.22, 3099–3108 (1973).
13. Fowler, A. V. & Zabin I. J.Biol.Chem.258, 14354–14358 (1983)
14. Rousset, J. P. Gilson, E. & Hofnung M. J.Mol.Biol. 191, 313–320 (1986)
15. Cervantes-Olivier. P. Delavier-Klutchko, C. Durieu-Trautmann, O. Kaveri, S. Desmandril, M. & Strosberg, A. D. Biochem. J. Biochem J 250:133–143.
16. Laemmli, U. K. & Favre M. J.Mol. Biol. 80, 575–599 (1973)
17. Reddy. P. Miller, D. & Peterkofsky, A. J.Biol. Chem. 261, 11448–11451 (1986).
18. Stiles, G. Arch. Biochem. Biophys. 237, 65–71 (1985)
19. Cervantes-Olivier. P. Durieu-Trautmann, O. Delavier-Klutchko, C. & Strosberg, A. D. Biochemistry 24, 3765–3770 (1985).
20. Hanada, K. Yamato, I. & Anraku, Y. J.Biol. Chem. 262, 14100–14104 (1987).
21. Allen M. Spiegel, Signal transduction by guanine nucleotide binding proteins; Molecular and Cellular Endocrinology, 49(1987)1–16 Elsevier Scientific Publishers Ireland, Ltd.
22. Marullo, S. et al.Proc.Natl.Acad.Sci.USA.85:7551–7555.1987
23. Boulain, J. C. et al.1986.Mutagenesis by random linker insertion into the lamB gene of Escherichia coli K12.

TABLE II

| ligands | E. coli Huβ1AR | E. coli Huβ2AR | E. coliKiβ1/Kiβ2 | mamm. β1AR | mamm. β2AR | mamm. β1/β2 |
|---|---|---|---|---|---|---|
| 1 epinephrine | 696 | 861 | 0,81 | 1900 | 403 | 4,7 |
| 2 norepinephrine | 345,3 | 4805 | 0,07 | 2800 | 1880 | 1,49 |
| 3 Isoproterenol | 38,2 | 134,8 | 0,28 | 236 | 110 | 2,14 |
| 4 procaterol | 4652 | 55,3 | 84,1 | — | — | — |
| 5 propranolol | 5,3 | 0,81 | 6,5 | 2,99 | 0,54 | 5,5 |
| 6 ICI 118,551 | 304,3 | 2,74 | 111,1 | 86 | 0,66 | 130 |
| 7 CGP 20712-A | 3,54 | 7368 | 0,0005 | 3,24 | 982 | 0,003 |
| 8 clembuterol | 37 | 12 | 3,1 | 71 | 14 | 5,1 |
| 9 zinterol | 168 | 9,14 | 18,4 | 170 | 21 | 8,1 |
| 10 R67555 | 0,13 | 3,83 | 0,03 | 0,90 | 46 | 0,02 |
| 11 L-643717-01 | 0,56 | 130 | 0,004 | 3,53 | 192 | 0,02 |

REFERENCES

1. Frielle, T. Collins, S. Daniel, K. W. Caron, M. G. Lefkowitz, R. J. & Kobilka B. K. Proc.Natl. Acad. Sci. USA. 84.7920–7924(1987).

24. Charbit, A. et al. 1986.EMBO J.5:3029§3037.
25. Yanisch§Perron, C. et al. 1985-Gene.33.103–119.

26. In Current protocols in molecular biology.1989. Auzubel, F. M. et al. (Ed) Greene Publishing associates and Wiley§Interscience, NEW YORK.

What is claimed is:

1. A yeast cell stably transformed with an expression vector comprising:
   (a) an insert encoding a polypeptide of a mammalian receptor comprising seven hydrophobic transmembrane segments, extracellular and intracellular loops, an extracellular amino terminal region, and a carboxyl terminal cytoplasmic region; and
   (b) a control region capable of being recognized by polymerases of the yeast cell for expression of said polypeptide in said yeast cell, wherein said control region comprises a signal sequence; and
   wherein, after expression, said polypeptide is incorporated into a cell membrane of said yeast cell and said polypeptide is capable of binding a ligand of said mammalian receptor.

2. The yeast cell as claimed in claim 1, wherein said signal sequence is an N-terminal sequence of a precursor of a protein of the yeast cell which is normally transported to the membrane of the yeast cell.

3. The yeast cell as claimed in claim 1, wherein said control region comprises an inducible promoter.

4. The yeast cell as claimed in claim 3, wherein said yeast cell is *S. cerevisiae*.

5. The yeast cell as claimed in claim 4, wherein said control region comprises a promoter which is an alcohol dehydrogenase I promoter or a galactokinase promoter.

6. A yeast cell stably transformed with an expression vector comprising:
   (a) an insert encoding a polypeptide of a mammalian receptor selected from the group consisting of β-adrenergic receptors and serotonin receptors; and
   (b) a control region capable of being recognized by polymerases of the yeast cell for expression of said polypeptide in said yeast, wherein said control region comprises a signal sequence; and
   wherein, after expression, said polypeptide is incorporated into the cell membrane of said yeast cell and said polypeptide is capable of binding a ligand of said mammalian receptor.

7. The yeast cell as claimed in claim 6, wherein said signal sequence is an N-terminal sequence of a precursor of a protein of the yeast cell which is normally transported to the membrane of the yeast cell.

8. The yeast cell as claimed in claim 6, wherein said control region comprises an inducible promoter.

9. The yeast cell as claimed in claim 8, wherein said yeast cell is *S. cerevisiae*.

10. The yeast cell as claimed in claim 9, wherein said control region comprises an alcohol dehydrogenase I promoter or galactokinase promoter.

11. A yeast cell stably transformed with an expression vector comprising:
    (a) an insert encoding a mammalian receptor comprising seven hydrophobic transmembrane segments, extracellular and intracellular loops, an extracellular amino terminal region, and a carboxyl terminal cytoplasmic region; and
    (b) a control region capable of being recognized by polymerases of the yeast cell for expression of said polypeptide in said yeast cell; and
    wherein, after expression, said polypeptide is incorporated into a cell membrane of said yeast cell and said polypeptide is capable of binding a ligand of said mammalian receptor.

12. The yeast cell as claimed in claim 11, wherein said control region comprises an alcohol dehydrogenase I promoter or a galactokinase promoter.

13. A yeast cell stably transformed with an expression vector comprising:
    (a) an insert encoding a polypeptide of a mammalian receptor selected from the group consisting of β-adrenergic receptors and serotonin receptors; and
    (b) a control region capable of being recognized by polymerases of the yeast cell for expression of said polypeptide in said yeast cell; and
    wherein, after expression, said polypeptide is incorporated into a cell membrane of said yeast cell and said polypeptide is capable of binding a ligand of said mammalian receptor.

14. The yeast cell as claimed in claim 13, wherein said control region comprises an inducible promoter.

15. The yeast cell as claimed in claim 13, wherein said yeast cell is *S. cerevisiae*.

16. The yeast cell as claimed in claim 13, wherein said control region comprises an alcohol dehydrogenase I promoter or a galactokinase promoter.

17. A yeast cell stably transformed with a vector comprising a DNA sequence encoding a mammalian G protein-coupled receptor structurally related to the mammalian β-adrenergic receptor, the 5' end of said sequence being functionally joined to and in proper reading frame with the 3' end of the sequence encoding the amino terminal end of a protein normally functional in said yeast cell wherein said yeast cell expresses on its surface said G protein-coupled receptor having seven transmembrane segments.

18. The yeast cell as claimed in claim 17, wherein said mammalian β-adrenergic receptor is a β1-adrenergic receptor.

19. The yeast cell as claimed in claim 17, wherein said mammalian β-adrenergic receptor is a β2-adrenergic receptor.

20. The yeast cell according to claim 17, wherein said yeast cell is *S. cerevisiae*.

21. A *S. cerevisiae* organism stably transformed with a vector comprising a DNA sequence encoding a mammalian G protein-coupled receptor structurally related to the mammalian β-adrenergic receptor, the 5' end of said sequence being functionally joined to and in proper reading frame with the 3' end of the sequence encoding the amino terminal end of a protein normally functional in said yeast cell wherein said yeast cell expresses on its surface said G protein-coupled receptor having seven transmembrane segments.

* * * * *

UNITED STATES PATENT AND TRADEMARK OFFICE
CERTIFICATE OF CORRECTION

PATENT NO.   : 6,645,755 B1
DATED        : November 11, 2003
INVENTOR(S)  : Stefano Marullo et al.

It is certified that error appears in the above-identified patent and that said Letters Patent is hereby corrected as shown below:

<u>Column 17,</u>
Line 56, "encoding a" should read -- encoding a polypeptide of a --.

Signed and Sealed this

Twenty-seventh Day of January, 2004

JON W. DUDAS
*Acting Director of the United States Patent and Trademark Office*